United States Patent [19]

Johnson

[11] Patent Number: 5,869,653
[45] Date of Patent: Feb. 9, 1999

[54] HYDROGENATION OF NITRILES TO PRODUCE AMINES

[75] Inventor: Thomas Albert Johnson, Orefield, Pa.

[73] Assignee: Air Products and Chemicals, Inc., Allentown, Pa.

[21] Appl. No.: 960,909

[22] Filed: Oct. 30, 1997

[51] Int. Cl.$^6$ .................. C07D 223/10; C07D 211/76; C07D 207/24; C07C 273/18; C07C 231/12; C07C 209/48

[52] U.S. Cl. .................. 540/531; 546/243; 548/550; 564/59; 564/224; 564/385; 564/415; 564/490; 564/491; 564/492; 564/493

[58] Field of Search .................. 540/531; 546/243; 548/550; 564/59, 224, 385, 415, 490, 491, 492, 493

[56] References Cited

U.S. PATENT DOCUMENTS

| | | | |
|---|---|---|---|
| 3,223,735 | 12/1965 | Scholz et al. | 260/583 |
| 3,427,356 | 2/1969 | Baer et al. | 260/583 |
| 3,821,305 | 6/1974 | Bartalini et al. | 260/583 K |
| 4,375,003 | 2/1983 | Allain et al. | 564/492 |
| 5,075,507 | 12/1991 | Carr et al. | 564/491 |
| 5,254,737 | 10/1993 | Zimmerman | 564/490 |

*Primary Examiner*—Michael G. Ambrose
*Attorney, Agent, or Firm*—Russell L. Brewer

[57] ABSTRACT

An improved process for the catalytic hydrogenation of nitriles. The basic process comprises contacting the nitrile with hydrogen in the presence of a sponge or Raney cobalt catalyst under conditions for effecting conversion of the nitrile group to the primary amine. The improvement in the hydrogenation process resides in effecting the hydrogenation in the presence of a catalytic amount of lithium hydroxide and water. To achieve a catalytic amount of lithium hydroxide, the catalyst may be pretreated with the lithium hydroxide and/or the reaction may be carried out with the lithium hydroxide present in the reaction medium.

24 Claims, No Drawings

HYDROGENATION OF NITRILES TO PRODUCE AMINES

BACKGROUND OF THE INVENTION

One method the industry currently uses to manufacture aliphatic amines is the catalytic hydrogenation of aliphatic nitrites, e.g., cyanoethylated amines in either batch or trickle bed hydrogenation equipment. To selectively form primary amines such as dimethylaminopropyl amine (DMAPA) from the precursor nitrile, ammonia is generally used to control the ratio of primary to secondary amine. However, substantial amounts of ammonia are needed to be effective, and even then, several percent of secondary amine coproduct is formed. The handling of ammonia is expensive in that it requires pressurized storage, increases cycle time for loading and venting and it can present an environmental problem unless expensive recovery equipment is provided. Thus, there has been a desire to find ways to effect the hydrogenation of nitrites without the use of ammonia.

Representative patents which illustrate various procedures for the catalytic hydrogenation of nitrites are as follows:

U.S. Pat. No. 4,375,003 discloses a catalytic process for preparing amines by reacting an aliphatic nitrile and hydrogen in the presence of a sponge cobalt catalyst. The improved catalysts employed for the hydrogenation of the aliphatic nitriles are based upon cobalt-aluminum alloys which have been contacted with an alkali metal hydroxide dispersed in an aqueous medium. The examples show the addition of sodium hydroxide solutions to the cobalt-aluminum alloy which catalyst is then used to catalyze the hydrogenation reaction.

U.S. Pat. No. 3,821,305 discloses a process for the catalytic hydrogenation of the adiponitrile to form hexamethylenediamine by carrying out the hydrogenation in the presence of a sponge catalyst and caustic alkali where the hydrogen and the adiponitrile are fed into a liquid reaction medium consisting of hexamethylenediamine, water and the caustic alkali and catalyst. The catalyst employed is a sponge nickel catalyst. The examples show the use of sodium hydroxide as the caustic alkali.

U.S. Pat. No. 3,223,735 discloses a process for the catalytic hydrogenation of a reaction product of acrylonitrile and ammonia to form 1,3-propylene diamine. A wide variety of group Vb, Vlb, Vllb and Vlllb metals are taught as being suited for practicing the hydrogenation process. A large excess of ammonia is used in the process to avoid the formation of secondary amines.

U.S. Pat. No. 5,075,507 discloses a process for the cyanoethylation of glycols to produce bis(cyanoethylated) aliphatic glycols followed by reaction with hydrogen to form bis(aminopropyl)aliphatic glycols. In terms of effecting the reduction of the cyano group of the cyanoethylated glycol, the hydrogenation is carried out using a hydrogenation catalyst such as sponge nickel, palladium, platinum, ruthenium, rhodium and cobalt. Ammonia is charged to the reaction medium to maintain high yield and selectivity.

U.S. Pat. No. 3,427,356 discloses a process for producing 1,3-propylene diamines using cobalt or nickel catalysts. The improvement in their process involves the addition of a small amount of manganese dissolved in the reaction medium.

U.S. Pat. No. 5,254,737 discloses a continuous process for preparing secondary amines from nitriles. The secondary amines are prepared by carrying out the reactions in the presence of ammonia and hydrogen in the first stage and then effecting hydrogenation in the absence of ammonia. The catalyst employed in the reaction is either nickel or cobalt.

BRIEF SUMMARY OF THE INVENTION

This invention is directed to an improved process for the catalytic hydrogenation of nitrites and to a unique catalyst for effecting the hydrogenation. The basic process comprises contacting the nitrile with hydrogen in the presence of a sponge or Raney cobalt catalyst under conditions for effecting conversion of the nitrile group to the primary amine. The improvement in the hydrogenation process resides in effecting the hydrogenation in the presence of a sponge cobalt catalyst incorporating from 0.1 to 100 millimoles lithium hydroxide per gram catalyst. To achieve a catalytic amount of lithium hydroxide in the sponge cobalt, the sponge cobalt catalyst may be pretreated in a solvent with lithium hydroxide preferably dissolved in water or the reaction may be carried out with the lithium hydroxide, preferably dissolved in water and dispersed in the reaction medium.

The invention is particularly suited for the hydrogenation of simple aliphatic and aromatic nitriles and dinitriles and those derived by the cyanoethylation of primary and secondary amines, the cyanoethylation agent being acrylonitrile. Examples of preferred nitrites are acetonitrile and 3-dimethylaminopropionitrile (DMAPN) which is obtained by the reaction of acrylonitrile and dimethylamine.

There are several advantages associated with the improved process and these include:

- an ability to achieve high production rates of primary amine;
- an ability to effect conversion of the nitrile group to the primary amine in high selectivity thus avoiding secondary amine formation as contemplated by prior processes;
- an ability to eliminate the need for ammonia and its associated problems; and
- an ability to use the catalyst over an extended time.

DETAILED DESCRIPTION OF THE INVENTION

A wide variety of nitrites may be used in the hydrogenation process, and these range from $C_{1-30}$ aliphatic to $C_{7-15}$ aromatic nitriles. Examples of aliphatic nitriles include $C_{1-30}$, preferably $C_{1-20}$ alkyl nitrites such as, adiponitronitrile, propionitrile, butyronitrile, lauronitrile, and stearonitrile; dinitriles such as adiponitronitrile, methylglutaronitrile and succinonitrile; cyclic nitrites such as isophoronenitrile; α-aminonitriles such as aminoacetonitrile, imino-bis-acetonitrile and nitrilotriacetonitrile, cyanoethylethers formed by reaction of acrylonitrile with alcohols, glycols or glycol ethers, such as methoxypropionitrile, biscyanoethylether, bis-(2-cyanoethyl)ethyleneglycol, bis-(2-cyanoethyl) diethyleneglycol, mono-(2-cyanoethyl)diethyleneglycol, and bis(2-cyanoethyl)tetramethyleneglycol, ether nitriles represented by the formula R—O(—CHR'CHR'—O)$_n$—CH$_2$–CH$_2$CN where R=, $C_1$–$C_{30}$ alkyl, R'=, $C_2$ –$C_8$ alkyl, n=1–20, β-unsaturated nitriles such as acrylonitrile, and β-aminonitriles formed by the reaction of acrylonitrile and $C_{1-30}$ alkyl and $C_{18}$ alkanolamines. Representative examples of β-aminonitriles are: β-aminopropionitrile, di-(2-cyanoethyl)amine, N-methyl-β-aminopropionitrile, N,N-dimethyl-β-aminopropionitrile, N-(2-cyanoethyl)ethanolamine, N,N-di-(2-cyanoethyl)ethanolamine, N-(2-cyanoethyl)diethanolamine and N-(2-cyanoethyl)propanolamine.

Other nitriles are based upon β-cyanoethylated urea, amides and lactams. The cyanoethylated urea is represented by the formula $R_2NCONR_2$ where $R=H$, $C_1$–$C_8$ alkyl radical or $CH_2CH_2CN$. N-cyanoethyl urea is an example. Cyanoethylated amides are represented by the formula; $RCON(CH_2CH_2CN)_n$ where R is H or a $C_{1-8}$ alkyl radical and n is 1 or 2. Examples include cyanoethylated acetamide, cyanoethylated propionamide and so forth.

Representative cyanoethylated lactams are represented by the formula: $(CH_2)_m CONCH_2CH_2CN$ where m is 3, 4 or 5. N-cyanoethyl caprolactam is an example.

Representative aromatic nitriles include: benzyl cyanide, benzonitrile, isophthalonitrile and terephthalonitrile.

A key to effectiveness of the hydrogenation process is to incorporate an effective amount of lithium hydroxide in the sponge cobalt catalyst to enhance the selectivity of the reaction. To minimize secondary amine formation, high selectivity is maintained by adding the lithium hydroxide in an amount of about 0.1 to 100 mmole/g of sponge cobalt catalyst. Preferably, the lithium hydroxide is added to provide a level of from 2 to 30 mmole/g of catalyst.

The cobalt catalyst used in the hydrogenation process is sponge cobalt, or as it is sometimes called, Raney cobalt. One method of preparing the lithium hydroxide modified sponge cobalt catalyst is by adding an aqueous lithium hydroxide solution to a slurry of the cobalt catalyst carried in the reaction medium. In the alternative, the catalyst may be prepared prior to introduction to the reaction medium. This treatment can be accomplished by first slurrying the sponge cobalt in the presence of a water miscible, or at least partially miscible solvent but one in which the lithium hydroxide is largely insoluble. The water miscible or partially miscible solvent may be an amine, typically the amine product to be produced in the reaction vessel, an ether such as tetrahydrofuran or diglyme; an amide such as N,N-dimethylformamide or N,N-dimethylacetamide, a nitrile, preferably the nitrile to be hydrogenated, then adding the aqueous hydroxide solution in an amount from about 0.1 to 100 mmole/g of catalyst, preferably 2 to 30 mmole/g of catalyst. The catalyst is stirred for 1 to 60 minutes, preferably for 2 to 30 minutes, at ambient conditions. The solvent may be decanted from the treated catalyst or removed by filtration. Preferably, this is effected while under an inert atmosphere, e.g., nitrogen or a solvent. The lithium hydroxide tends to become bound or incorporated onto the surface or within the pores of the sponge cobalt on contact. If water is the sole medium in which the sponge cobalt is contacted, the lithium hydroxide will substantially be removed from the catalyst on filtration.

Conventional promoters may be present in the sponge cobalt the catalyst in conventional amounts. Examples of promoters include Group VIa and Group VIII metals such as chromium, iron, molybdenum, nickel and so forth.

The hydrogenation process is conducted under conditions such that the water concentration in the reactor is maintained between about 0.1% by weight but less than 25%, preferably between 0.3 and 8% by weight of the nitrile to be hydrogenated. The presence of water assists in maintaining catalyst activity.

The reduction of the nitrile to the amine is carried out under a hydrogen pressure of from 1 to 300 bars, typically from 5 to 80 bars, and at temperatures of from about 60° to 160° C. Typical batch reaction times range from 15 to 600 minutes.

The hydrogenation also can be conducted in conventional hydrogenation equipment, e.g., a stirred tank or loop reactor, a continuous stirred tank reactor, a continuous gas lift reactor, a fixed-bed plug flow reactor, a trickle-bed reactor, a bubble column reactor or a sieve-tray reactor. Preferred methods of operation include semi- batch and continuous back-mix.

The following examples are provided to illustrate various embodiments of the invention and are not intended to limit the scope thereof.

EXAMPLE 1

Hydrogenation of 3-Dimethylaminopropionitrile over Unpromoted Sponge Cobalt in the Presence of Lithium Hydroxide In a 2 liter autoclave containing a stirrer, cooling coil and filter tipped sample tube for sampling was added 606.4 g of 3-dimethylaminopropionitrile (DMAPN), 6.0 g (7.5 mmole/g catalyst) of lithium hydroxide monohydrate dissolved in 58.5 g water (total water content, 8.89%), and 18.1 g (2.63% by weight) unpromoted sponge cobalt (W. R. Grace, type 2700). After purging the autoclave with nitrogen and then hydrogen, the reaction was pressurized to 75 psig and heated to 100° C. while stirring at 50 rpm. At 100° C. the pressure was increased to 850 psig and the stirrer speed to 900 rpm. Although the hydrogen uptake appeared to stop after about 1 hour, the reaction mass was allowed to remain at these conditions for another 30 minutes before cooling to room temperature for venting and discharge. Samples were taken periodically during the reaction and the progress of the reaction is shown in Table 1.

TABLE 1

Normalized Weight Percent (Water-free Basis)

| time min | dma wt % | mnpa wt % | dmapa wt % | dmapn wt % | tmpda ppm | 2°amine wt % | 2°imine wt % | others wt % |
|---|---|---|---|---|---|---|---|---|
| 0 | 0.124 | 0.007 | 0.244 | 98.635 | 47 | 0.025 | 0.120 | 0.841 |
| 13 | 0.304 | 0.068 | 12.012 | 85.365 | 54 | 0.036 | 0.211 | 1.999 |
| 23 | 0.453 | 0.174 | 28.325 | 68.078 | 90 | 0.074 | 0.501 | 2.386 |
| 31 | 0.555 | 0.305 | 44.456 | 51.295 | 75 | 0.105 | 0.751 | 2.525 |
| 41 | 0.646 | 0.442 | 59.318 | 35.887 | 81 | 0.128 | 0.794 | 2.777 |
| 51 | 0.704 | 0.592 | 77.583 | 17.222 | 82 | 0.154 | 0.809 | 2.928 |
| 61 | 0.695 | 0.650 | 90.409 | 4.149 | 82 | 0.535 | 0.479 | 3.075 |
| 93 | 0.701 | 0.665 | 93.849 | 0.531 | 87 | 0.842 | 0.232 | 3.171 | dma = dimethylamine
mnpa = mono-n-propylamine
dmapa = 3-dimethylaminopropylamine
dmapn = 3-dimethylaminopropionitrile
tmpda = N,N,N',N'-tetramethyl-1,3-propanediamine
2°amine = di-(3-dimethylaminopropyl)amine
2°imine = N-(3-dimethylaminopropylidene)-3-dimethylaminopropylamine
others = unidentified components Example 1 shows the in situ catalyst preparation in the presence of the nitrile reaction medium. Table 1 shows that the amount of secondary amine remained below 1% and the tmpda remained well below 300 ppm by weight when dmapn was hydrogenated utilizing a sponge cobalt catalyst and carrying out the reaction in the presence of a lithium hydroxide/water medium. The reaction rate was excellent with 99.5% conversion in 1 and ½ hours.

EXAMPLE 2

Hydrogenation of 3-Dimethylaminopropionitrile over Promoted Sponge Cobalt in the Presence of Lithium Hydroxide To the same equipment described in Example 1 was added 693 g of 3-dimethylaminopropionitrile, 6.9 g (0.92% by weight) of promoted sponge cobalt (W. R. Grace, type 2724) and 3.6 g (11.9 mmole/g catalyst) of lithium hydroxide monohydrate dissolved in 41.2 g of water (total water content, 5.73%). The reaction was conducted as in Example 1 but at 750 psig rather than 850 psig. The results are shown in Table 2.

TABLE 2

Normalized Weight Percent (Water-free Basis)

| time min | dma wt % | mnpa wt % | dmapa wt % | dmapn wt % | 3mpda wt % | tmpda ppm | 2°imine wt % | 2°amine wt % |
|---|---|---|---|---|---|---|---|---|
| 93 | 0.321 | .0204 | 97.108 | 0.044 | 0.015 | 48 | 0.225 | 2.078 |

3mpda = N,N,N'-trimethyl-1,3-propanediamine
See Table 1 for identification of other acronyms.

Note that the amount of TMPDA produced after a reaction time of 93 minutes was less than the 300 ppm as was the case in Example 1 and the amount of secondary amine was also low. The conversion was higher even though the hydrogen pressure was lower and the amount of catalyst only about ⅓ as much. These improvements over Example 1 are attributed to the presence of promoters in the lithium hydroxide treated sponge cobalt catalyst.

EXAMPLE 3 TO 6

Hydrogenation of 3-Dimethylaminopropionitrile with Reuse of the Lithium Hydroxide Treated Sponge Cobalt Catalyst After the reaction mixture from Example 2 was cooled, all but about 5% of the liquid phase was filtered through a sample tube which had been fitted with a sintered stainless steel element. The catalyst remained inside the reactor. Another charge of 3-dimethylaminopropionitrile was then added as was enough water to bring the water concentration based of the amount of DMAPN to about 3 wt %. The freshly charged DMAPN was then hydrogenated as in Example 2. No additional lithium hydroxide was added. This procedure was repeated a total of 6 times, recycling the catalyst and lithium hydroxide a total of seven times before the termination of the series of experiments.

Table 3 shows the amount of DMAPN and water added as well as the reaction conditions used for each experiment. The variables used to control the reaction rate for these experiments were agitation speed and/or pressure. Those results are shown in Table 4.

TABLE 3

Charge Size and Conditions for Examples 2 to 6

| Ex. | catalyst use | pressure (psig) | agitation (rpm) | temp. (°C.) | dmapn (g) | water (g) | water (wt %) | catalyst (g) | LiOH.H$_2$O (g) |
|---|---|---|---|---|---|---|---|---|---|
| 2 | 1 | 750 | 900 | 100 | 693.0 | 41.2 | 5.6 | 6.9 | 3.6 |
| 3 | 2 | 750 | 400–610 | 100 | 879.7 | 26.7 | 3.0 | 6.9* | 3.6* |
| 4 | 4 | 150–550 | 1200 | 100 | 853.0 | 27.3 | 3.1 | 6.9* | 3.6* |
| 5 | 5 | 200–625 | 1200 | 100 | 853.6 | 26.4 | 3.0 | 6.9* | 3.6* |
| 6 | 7 | 300–750 | 1200 | 100 | 897.5 | 32.6 | 3.5 | 6.9* | 3.6* |

*Recycled from previous batch

See Table 1 for identification of acronyms.

TABLE 4

Results of Examples 2 to 6
Normalized Weight Percent (Water-free Basis)

| Ex. | catalyst use | reaction time (min) | dma (wt %) | mnpa (wt %) | dmapa (wt %) | dmapn (wt %) | tmpda (ppm) | 2°imine (wt %) | 2°amine (wt %) |
|---|---|---|---|---|---|---|---|---|---|
| 2 | 1 | 93 | 0.321 | 0.204 | 97.108 | 0.044 | 48 | 0.225 | 2.078 |
| 3 | 2 | 290 | 0.365 | 0.275 | 95.321 | 0.008 | 56 | 0.208 | 3.798 |
| 4 | 4 | 285 | 0.335 | 0.281 | 97.166 | 0.021 | 61 | 0.198 | 1.992 |
| 5 | 5 | 315 | 0.346 | 0.297 | 97.337 | 0.027 | 63 | 0.2 est | 1.986 |
| 6 | 7 | 325 | 0.353 | 0.310 | 97.283 | 0.064 | 63 | 0.211 | 1.592 |

See Table 1 for identification of acronyms.

It is clear from the data that regardless of how the reaction was controlled, the amount of TMPDA was essentially unaffected. On the other hand, the amount of secondary amine (2°amine) formed was dependent upon the reaction conditions and in particular by the agitation speed (see Example 2). Pressure did not seem to strongly affect the selectivity. Aging of the catalyst was very slow under these conditions and even though it took longer and required somewhat higher pressure to finish, the selectivity did not appear to deteriorate in any appreciable way.

Note that lithium hydroxide was only added in Example 2. No lithium hydroxide was added to Examples 3 to 6 and yet the selectivity to 2°amine and TMPDA was essentially unchanged (particularly note Examples 4, 5 and 6 where 2°amine appears to actually decrease and TMPDA remains constant). Thus, one can conclude that once the catalyst has been treated with lithium hydroxide its effect appears to be permanent and the catalyst remains active unless contaminated.

EXAMPLES 7 TO 21

Hydrogenation of 3-Dimethylaminopropionitrile with Reuse of the Lithium Hydroxide Treated Sponge Cobalt Catalyst—Catalyst Life Study The purpose of this example was to determine catalyst life of the sponge cobalt catalyst.

Fifteen charges of 3-dimethylaminopropylamine was manufactured in commercial scale equipment charged with 96.4% 3-dimethylaminopropionitrile, 0.4% promoted sponge cobalt (W. R. Grace, type 2740), 0.2% lithium hydroxide monohydrate (11.4 mmole/g catalyst) and 2.37% water, at a hydrogen pressure of from 371 to 578 psig and with high shear agitation and with an average reaction time of 260 minutes at 70° to 130° C. As in Examples 2–6, the lithium hydroxide and catalyst were added to only the first charge.

Table 5 sets forth the conditions and results.

TABLE 5

Results of Examples 7 to 21
Normalized Weight Percent (Water-free Basis)

| Example | catalyst use | reaction time (hr) | dmapa (wt %) | 2° amine (wt %) |
|---|---|---|---|---|
| 7 | 1 | 3.5 | 97.86 | 1.32 |
| 8 | 2 | 5.25 | 97.72 | 1.54 |
| 9 | 3 | 5.5 | 98.07 | 1.15 |
| 10 | 4 | 3.75 | 98.15 | 1.11 |
| 11 | 5 | 3.75 | 96.57 | 1.73 |
| 12 | 6 | 4.25 | 97.72 | 1.39 |
| 13 | 7 | 4.25 | 97.44 | 1.20 |
| 14 | 8 | 4.75 | 97.36 | 1.34 |
| 15 | 9 | 4.75 | 98.03 | 1.32 |
| 16 | 10 | 4.25 | 97.46 | 1.58 |
| 17 | 11 | 4.75 | 96.54 | 1.89 |
| 18 | 12 | 5.25 | 97.10 | 1.79 |
| 19 | 13 | 3.75 | 96.95 | 1.81 |
| 20 | 14 | 3.5 | 96.15 | 1.86 |
| 21 | 15 | 3.75 | 97.09 | 1.67 |

See Table 1 for identification of acronyms.

Table 5 shows there is little if any deterioration in yield of DMAPA as a function of number of reuses of the catalyst and also that little if any increase in reaction time was needed to reduce the level of DMAPN to below 0.05% by weight. Also shown is how the secondary amine (2°amine) remained below 2% throughout.

EXAMPLE 22–32

Hydrogenation of 3-Dimethylaminopropionitrile Over Lithium Hydroxide Treated Sponge Cobalt Catalyst Effect of Temperature, Pressure and Water To the same equipment described in Example 1 was added 732.5 g of 3-dimethylaminopropionitrile, 3.92 g (0.52% by weight) of promoted sponge cobalt (W. R. Grace, type 2724) and 1.63 g (9.5 mmole/g of catalyst) of lithium hydroxide monohydrate dissolved in 19.73 g of water (total water content, 2.74%). The reaction was conducted as in Example 1 but at 400 psig rather than 850 psig and the reaction temperature was programmed from 70° to 100° C. such that the hydrogen consumption rate was essentially constant and that about 99% of theory of the hydrogen was consumed in about 180 minutes and then the reaction mixture allowed to remain at the final conditions for another 30 to 100 minutes. The reaction product was then removed through the filter tube, another charge of DMAPN and water added and the next run commenced. After the reaction time appeared to increase under these conditions, the pressure was raised to 750 psig.

In Example 26, the original stock of DMAPN ran out and a second lot was mixed with the first to complete the charge. In Example 27 to 32 the second lot of DMAPN was used exclusively. This second lot of DMAPN contained 895 ppm of TMPDA as a contaminant.

In Example 31, only DMAPN was charged, but no water added. In addition the maximum temperature was raised to 120° C. after about ¾ of the hydrogen had been consumed and then to 140° C. after 99% was consumed. In Example 32, only DMAPN was added and the entire run was conducted at 140° C. and a hydrogen pressure from 400 to 440 psig. The lower pressure slowed the reaction down but even at this low pressure the reaction was essentially finished in 135 minutes, thus showing an excellent reaction rate.

As a result, the amount of TMPDA actually produced during the hydrogenation must be corrected by subtracting 895 ppm from the total amount measured at the end of the hydrogenation reaction. The results are shown in Table 7.

TABLE 7

Results from Examples 22 to 32

| Example | 22 | 23 | 24 | 25 | 26 | 27 | 28 | 29 | 30 | 31 | 32 |
|---|---|---|---|---|---|---|---|---|---|---|---|
| catalyst use | 1 | 2 | 3 | 4 | 5 | 6 | 7 | 8 | 9 | 10 | 11 |
| temp (°C.) | 70–100 | 80–100 | 80–100 | 80–101 | 85–100 | 90–100 | 100 | 100 | 100 | 100–140 | 140 |
| press (psig) | 400 | 400 | 400 | 400 | 400 | 400 | 750 | 750 | 750 | 750 | 400–440 |
| rpm | 1200 | 1200 | 1200 | 1200 | 1200 | 1200 | 1200 | 1200 | 1200 | 1200 | 1200 |
| catalyst % | 0.52 | 0.52 | 0.52 | 0.52 | 0.52 | 0.52 | 0.52 | 0.52 | 0.52 | 0.52 | 0.52 |
| dmapn % | 96.67 | 96.27 | 96.27 | 96.27 | 96.27 | 96.27 | 96.27 | 96.27 | 96.27 | 98.97 | 98.97 |
| water % | 2.6 | 3.0 | 3.0 | 3.0 | 3.0 | 3.0 | 3.0 | 3.0 | 3.0 | 0.3 | 0.3 |
| LiOH.H2O % | 0.21 | 0.21 | 0.21 | 0.21 | 0.21 | 0.21 | 0.21 | 0.21 | 0.21 | 0.21 | 0.21 |
| rx time (min) | 290 | 220 | 295 | 280 | 295 | 340 | 265 | 240 | 275 | 300 | 135 |
| Composition (wt %) | | | | | | | | | | | |
| dma | 0.117 | 0.166 | 0.180 | 0.209 | 0.327 | 0.922 | 0.872 | 0.928 | 0.940 | 0.694 | 0.947 |
| mnpa | 0.101 | 0.164 | 0.201 | 0.234 | 0.273 | 0.304 | 0.229 | 0.250 | 0.267 | 0.109 | 0.461 |
| dmapa | 98.547 | 98.104 | 97.822 | 97.631 | 97.423 | 96.813 | 97.453 | 97.407 | 97.342 | 98.072 | 96.592 |
| dmapn | 0.025 | 0.026 | 0.012 | 0.009 | 0.033 | 0.012 | 0.016 | 0.042 | 0.035 | 0.080 | 0.381 |
| tmpda (ppm) | 40 | 38 | 59 | 99 | 165 | 928 | 978 | 995 | 991 | 1049 | 1138 |
| corrected tmpda (ppm) | 40 | 38 | 59 | 99 | | 33 | 83 | 100 | 96 | 154 | 243 |
| 2°imine | 0.195 | 0.154 | 0.185 | 0.188 | 0.185 | 0.184 | 0.177 | 0.183 | 0.182 | 0.167 | 0.126 |
| 2°amine | 0.781 | 1.012 | 1.245 | 1.283 | 1.333 | 1.319 | 0.882 | 0.831 | 0.848 | 0.534 | 0.939 |
| other | 0.229 | 0.369 | 0.349 | 0.435 | 0.409 | 0.354 | 0.274 | 0.259 | 0.286 | 0.238 | 0.440 |

See Table 1 for identification of acronyms.

See Table 1 for identification of acronyms.

Here, as in Examples 7 to 21, we see that the selectivity to primary amine (DMAPA) remained very high, the amount of TMPDA remained well under 300 ppm and the secondary amine never reached 1.5% throughout 11 uses of the catalyst even though the temperature was varied from 70° to 140° C., the pressure from 400 to 750 psig and the water content from 0.3 to 3 wt %. Surprisingly, this was accomplished with only 0.5% of catalyst and 9.2 mmole LiOH/g of catalyst present.

EXAMPLES 33 AND 34

Hydrogenation of 3-Dimethylaminopropionitrile Over Promoted Sponge Cobalt Catalyst In The Presence Of Water And Absence Of LiOH To the same equipment described in Example 1 was added 865 g of 3-dimethylaminopropionitrile (contaminated with 895 ppm TMPDA), 4.61 g (0.51% by weight) of promoted sponge cobalt (W. R. Grace, type 2724) and 31.0 g of water (3.4%). The reaction was conducted as in Example 22 but over a temperature range from 60° to 100° C. and 400 psig. After the reaction was complete, the product was removed through the filter tipped sample tube, leaving the catalyst behind. A second charge of DMAPN was then added and a the hydrogenation effected at 750 psig. Table 8 shows the results of these two reactions.

TABLE 8

Results from Examples 33 and 34

| Example | 33 | 34 |
|---|---|---|
| catalyst use | 1 | 2 |
| temp (°C.) | 60–100 | 75–100 |
| press (psig) | 400 | 750 |
| rpm | 1200 | 1200 |
| catalyst % | 0.51 | 0.57 |
| dmapn % | 96.05 | 96.58 |
| water % | 3.44 | 2.86 |
| LiOH*H2O % | 0 | 0 |

TABLE 8-continued

Results from Examples 33 and 34

| Example | 33 | 34 |
|---|---|---|
| rx time (min) | 390 | 260 |
| Composition (wt %) | | |
| dma | 1.566 | 1.215 |
| mnpa | 0.273 | 0.285 |
| dmapa | 77.976 | 81.993 |
| dmapn | 0.049 | 0.016 |
| tmpda (ppm) | 2160 | 2143 |
| corrected tmpda (ppm) | 1265 | 1348 |
| dmppda | 0.660 | 0.654 |
| 2° imine | 2.477 | 0.217 |
| 2° amine | 10.340 | 11.394 |
| 3° amine | 2.093 | 0.376 |
| long ret. unknown | 2.230 | 2.136 |
| others | 2.119 | 1.490 |

These results show that when lithium hydroxide is not used, large amounts of 2°amine and imine are formed as well as other assorted byproducts and the yield of DMAPA is reduced to 77–80%. The TMPDA amount, adjusted for TMPDA in the 10 DMAPN, is over 1200 ppm showing that lithium hydroxide is an important ingredient for controlling not only byproducts such as 2°amine but also for TMPDA.

EXAMPLE 35 AND 36

Hydrogenation of 3-Dimethylaminopropionitrile Over Promoted Sponge Cobalt Catalyst Pretreated With LiOH After releasing the pressure but before discharging the reactor in Example 34, a solution of 2.38 g (11.7 mmole/g of catalyst) of lithium hydroxide monohydrate in 20 ml of water was added, under a nitrogen atmosphere. The slurry of sponge cobalt in DMAPA then was stirred for 30 minutes. The DMAPA was then discharged from the reactor through the filter tipped sample tube.

Another charge of DMAPN and water was then added and the hydrogenation was conducted essentially as described in Example 34, i.e., at 750 psig and 80°–100° C., on the same catalyst but now treated with lithium hydroxide. After hydrogen consumption stopped, the reaction product was discharged through the filter tipped sample tube and a fourth charge of DMAPN and water added. This charge was hydrogenated in the same manner. Table 9 shows the results of these two examples.

TABLE 9

Results from Examples 35 and 36

| Example | 35 | 36 |
|---|---|---|
| catalyst use | 3 | 4 |
| temp (°C.) | 80–100 | 80–100 |
| press (psig) | 750 | 750 |
| rpm | 1200 | 1200 |
| catalyst % | 0.56 | 0.56 |
| dmapn % | 96.28 | 96.28 |
| water % | 2.98 | 2.99 |
| LiOH*H2O % | 0.29 | 0.29 |
| rx time (min) | 265 | 230 |
| Composition (wt %) | | |
| dma | 0.759 | 0.820 |
| mnpa | 0.109 | 0.142 |
| dmapa | 97.217 | 97.648 |
| dmapn | 0.013 | 0.045 |
| tmpda (ppm) | 1009 | 1093 |
| corrected tmpda (ppm) | 114 | 198 |
| dmppda | 0.036 | 0.008 |
| 2° imine | 0.186 | 0.169 |
| 2° amine | 1.200 | 0.840 |
| 3° amine | <.001 | <.001 |
| long ret. unknown | 0.142 | 0.017 |
| others | 0.237 | 0.200 |

It is obvious that the selectivity originally seen in Examples 1 to 32 was restored once lithium hydroxide was added to the catalyst. Further, the TMPDA concentration was also restored to levels below 300 ppm. Also, Example 35 shows that the catalyst may be pretreated with lithium hydroxide in a solvent such as DMAPA, simply by slurrying the catalyst in the solvent and an aqueous solution of the hydroxide in water at ambient temperature and pressure, but in an inert atmosphere.

COMPARATIVE EXAMPLE 37

Hydrogenation of 3-Dimethylaminopropionitrile Over Promoted Sponge Nickel

To the same equipment as described in Example 1 was charged 604 g of 3-dimethylaminopropionitrile, 6.11 g of chromium and iron promoted sponge nickel (Activated Metals, type A-4000) (0.905% by weight), and 6.33 g (23.5 mmole/g catalyst) lithium hydroxide monohydrate dissolved in 58.6 g of water (total water content was 9.0% by weight). The reaction was conducted as in Example 1. The results are shown in Table 10.

TABLE 10

Results of Comparative Example 37
Normalized Weight Percent (Water-free Basis)

| time (min) | dma | mnpa | dmapa | dmapn | tmpda (ppm) | 2°amine | 2°imine | others |
|---|---|---|---|---|---|---|---|---|
| 0 | 0.166 | 0.004 | 0.749 | 98.028 | 54 | 0.273 | 0.012 | 0.762 |
| 14 | 0.386 | 0.031 | 11.887 | 84.856 | 75 | 0.233 | 0.512 | 2.088 |
| 26 | 0.550 | 0.087 | 27.745 | 66.856 | 117 | 0.114 | 1.532 | 3.105 |
| 36 | 0.679 | 0.164 | 42.334 | 50.561 | 177 | 0.195 | 2.157 | 3.893 |
| 50 | 0.802 | 0.275 | 57.524 | 33.597 | 264 | 0.332 | 2.759 | 4.683 |
| 65 | 0.825 | 0.392 | 70.229 | 19.873 | 410 | 0.505 | 2.949 | 5.185 |
| 85 | 0.983 | 0.559 | 83.098 | 6.026 | 453 | 0.887 | 2.734 | 5.671 |
| 135 | 1.050 | 0.623 | 87.380 | 0.702 | 589 | 2.470 | 0.925 | 6.792 |

See Table 1 for identification of acronyms.

The results show that the DMAPN initially contained 54 ppm of TMPDA but as the reaction proceeded, the amount increased by 10 fold. The reaction was stopped after 135 minutes and there was still 0.7% of unreacted DMAPN present showing the reaction was slower than in Example 2 which was run under nearly identical conditions but with lithium hydroxide treated sponge cobalt catalyst. The sum of the 2°amine and 2°imine was 3.5% even though the amount of lithium hydroxide was double with respect to the catalyst that was used in Example 1. The amount of DMA, MNPA and other byproducts (others) was also very high in comparison to Example 1. This, however, was attributed to the large amount of water (9%) originally charged. Nevertheless, the yield of DMAPA was severely effected by these side reactions in comparison to the sponge cobalt/lithium hydroxide treated catalyst in Example 1.

COMPARATIVE EXAMPLE 38

Hydrogenation of 3-Dimethylaminopropionitrile with Recycled Sponge Nickel Catalyst As in Examples 3 to 6, the catalyst was separated from the reaction product via filtration and the reactor recharged with 602 g of 3-dimethylaminopropionitrile and 20 g of water. No additional lithium hydroxide or catalyst was charged. Table 11 sets forth the conditions and results.

The reaction time in Example 38 increased from 135 (Example 37) to 178 minutes to proceed to the same degree of conversion. Thus, a 32% loss of catalyst activity was indicated for promoted sponge nickel.

TABLE 11

Results of Comparative Example 38
Normalized Weight Percent (Water-free Basis)

| time (min) | dma | mnpa | dmapa | dmapn | tmpda (ppm) | 2°amine | 2°imine | others |
|---|---|---|---|---|---|---|---|---|
| 0 | 0.245 | 0.080 | 11.644 | 86.136 | 132 | 0.387 | 0.084 | 1.411 |
| 12 | 0.262 | 0.081 | 22.022 | 75.063 | 178 | 0.437 | 0.542 | 1.575 |
| 24 | 0.283 | 0.090 | 34.450 | 61.804 | 223 | 0.530 | 1.287 | 1.535 |
| 39 | 0.310 | 0.107 | 47.361 | 47.980 | 283 | 0.667 | 1.893 | 1.653 |
| 56 | 0.326 | 0.134 | 59.378 | 35.217 | 337 | 0.830 | 2.373 | 1.709 |
| 79 | 0.341 | 0.177 | 71.453 | 22.345 | 385 | 1.084 | 2.768 | 1.794 |
| 105 | 0.351 | 0.232 | 82.224 | 11.096 | 432 | 1.408 | 2.850 | 1.796 |
| 178 | 0.337 | 0.293 | 92.544 | 0.716 | 500 | 3.309 | 1.125 | 1.626 |

See Table 1 for identification of acronyms.

Since about 60 g of product from the previous example remained in the reactor and contained 589 ppm of TMPDA and 2.5% of 2°amine and almost 1% 2°imine, these impurities were initially present at higher levels than in Comparative Example 37. The total amount of water in this experiment was about 3% and this change resulted in far less generation of DMA, MNPA and other byproducts. It also resulted in there being less TMPDA made than in Comparative Example 37, however the amount was still much higher than that formed in Examples 1–6. And again, even though the initial amount of lithium hydroxide charged was twice that used in Examples 1–6 with respect to the amount of catalyst, the amount of 2°amine and imine was significantly higher, which is also a significant yield penalty.

COMPARATIVE EXAMPLE 39

Hydrogenation of 3-Dimethylaminopropionitrile With Recycled Catalyst—Sponge Nickel Catalyst Life Study Eight charges of 3-dimethylaminopropylamine were manufactured in commercial scale equipment charged with 96.4% 3-dimethylaminopropionitrile, 0.79% promoted sponge nickel (Activated Metals, Inc., type A-4000), 0.395% lithium hydroxide monohydrate and 2.37% water, at a hydrogen pressure of from 400 to 700 psig and with high shear agitation and with an average reaction time of 340 minutes at 70° to 110° C. Lithium hydroxide and catalyst were added to only the first charge. Table 12 sets forth the conditions and results.

TABLE 12

Normalized Weight Percent (Water-free Basis)

| comparative example | catalyst use | reaction time (min) | dmapa (wt %) | 2° amine (wt %) |
|---|---|---|---|---|
| 39 | 1 | 270 | 97.7 | 2.05 |
|  | 2 | 225 | 94.6 | 4.26 |
|  | 3 | 270 | 93.4 | 5.77 |
|  | 4 | 285 | 92.9 | 6.08 |
|  | 5 | 405 | 94.6 | 4.87 |
|  | 6 | 330 | 93.4 | 6.25 |
|  | 7 | 330 | 91.3 | 7.77 |
|  | 8 | 600 | 90.7 | 8.49 |

See Table 1 for identification of acronyms.

Table 12 shows the deterioration in yield as a function of number of reuses of the catalyst and also the increase in reaction time needed to reduce the level of DMAPN to below 0.2% by weight. Also shown is how the secondary amine (2°amine) increased as the catalyst aged. Comparing this data with that of Examples 7 through 21 in Table 5 one observes that lithium hydroxide treated sponge cobalt is much superior to lithium hydroxide treated sponge nickel under very similar conditions of operation in that the 2°amine concentration essentially stayed below 2 wt % throughout 15 uses of the catalyst and the yield of DMAPA was consistently over 96%. Furthermore, only ½ as much of the cobalt catalyst was used. On the other hand, in this example with lithium hydroxide treated sponge nickel, the 2°amine was never below 2% and it rose to 8.5% on eight uses indicating the lithium hydroxide had diminished more and more with each reuse. Furthermore the DMAPA yield decreased from 97.7% on the first use of the catalyst to 90.7% on the eight use.

COMPARATIVE EXAMPLE 40

Hydrogenation of 3-Dimethylaminopropionitrile Over NaOH Treated Sponge Cobalt A 2 liter Parr autoclave was charged with 538 g of 99+% pure 3-dimethylaminopropylamine (DMAPA), 10.5 g water, 5.3 g of sponge cobalt (W. R. Grace and Co., type 2724) and 1.55 g of sodium hydroxide (7.3 mmole/g). After purging out air with nitrogen, nitrogen with hydrogen and heating to 140° C. at a moderate hydrogen pressure, the pressure was raised to 58 barg, (bar gauge) the stirrer speed increased to 1200 rpm and 3-dimethylaminopropionitrile (DMAPN) was pumped in at a rate of 2.7 g/min (30.6 g DMAPN/g catalyst/hr, 55.1 meq/min; equiv. wt=98/2). Hydrogen was consumed at a rate of about 14.7 mmole/min indicating that significant DMAPN was accumulating in the reactor. A sample taken after 31 minutes showed that about 9.0% DMAPN had accumulated in the reactor and after another 34 minutes 18.4% DMAPN had accumulated. The pump was stopped and after another 190 minutes the DMAPN concentration decreased to 9.51 % which showed that the reaction was still proceeding but very slowly. The experiment was then terminated.

The secondary amine content at the time of the final sample had risen to 0.38% (not corrected for dilution by the heel) showing that although NaOH had prevented much secondary amine from forming, it did it so at the expense of reaction rate.

EXAMPLE 41

Hydrogenation of 3-Dimethylaminopropionitrile With Raney Cobalt Pretreated With LiOH In Example 40 the sponge cobalt catalyst was treated with NaOH which prior art teaches will strongly influence the selectivity of the reaction to minimize the generation of secondary amine without appreciably affecting the rate of reaction. Example 40 shows clearly that the reaction proceeded very slowly. To show that it was NaOH and not an inactive batch of catalyst that caused the poor performance, this experiment was conducted to test the catalyst activity. Thus, 5.77 g of sponge cobalt 2724 (W. R. Grace) and 0.498 g of LiOH·H$_2$O (2.05 mmole/g catalyst) were added to 403.69 g of a 99+% pure grade of 3-dimethylaminopropylamine in a 2 liter Parr autoclave. Enough water was added in transferring the catalyst to bring the water content to 2.9 wt %. The air was displaced with nitrogen and the nitrogen displaced with hydrogen and then heated to 140° C. under a positive hydrogen pressure. Once at 140° C. the hydrogen pressure was increased to 58 barg, the stirring speed increased to 1200 rpm and 3-dimethylaminopropionitrile (containing 2% water) was added using a high pressure pump at a rate of nominally 3, then 6, then 9 and finally 12 g/min. During each of these feed periods a sample was taken to monitor the residual DMAPN concentration. The data is shown in Table 13.

TABLE 13

Catalyst Activity Test
Sponge Cobalt Pretreated With LiOH/Water

| dmapn added (g) | dmapn rate (g/min) | dmapn rate (g/g/hr)* | dma | mnpa | dmapa | dmapn | tmpda | 2°amine | others |
|---|---|---|---|---|---|---|---|---|---|
| | | | | | Normalized Area % | | | | |
| 0 | 0.00 | 0 | 0.057 | 0.012 | 99.527 | 0.036 | 0.027 | 0.090 | 0.252 |
| 60 | 2.60 | 27 | 0.082 | 0.003 | 99.667 | 0.016 | 0.024 | 0.080 | 0.129 |
| 164 | 5.62 | 58 | 0.199 | 0.004 | 99.475 | 0.042 | 0.020 | 0.076 | 0.185 |
| 349 | 8.67 | 90 | 0.329 | 0.005 | 99.261 | 0.083 | 0.015 | 0.066 | 0.242 |
| 709 | 11.72 | 122 | 0.482 | 0.007 | 98.977 | 0.139 | 0.011 | 0.068 | 0.315 |

*Normalized rate = grams DMAPN/gram catalyst/hr

Table 13 shows that even at feed rates as high as 11.72 g/min (122 g/g/hr) that the hydrogenation reaction proceeded so fast when the sponge cobalt/lithium hydroxide treated catalyst was employed that the DMAPN concentration remained below 0.15%. Also, the selectivity with respect to primary and secondary amine was very highly in favor of primary amine. Even though dimethylamine concentration increased with the higher feed rate and higher DMAPN, the amount of TMPDA remained very low which also shows that these conditions also minimize byproduct formation resulting from reductive alkylation pathways. Another 641 g of DMAPN was then fed at 5.67 g/min and the DMAPN concentration remained below 0.056% showing little or no deactivation even though the catalyst had converted a total of 1350 g of DMAPN (235 g/g of catalyst) and the selectivity to secondary amine was still very low (actually dropped to 0.062%) as was the selectivity to TMPDA (dropped to 0.007%).

COMPARATIVE EXAMPLE 42

Effect of NaOH Addition To LiOH Promoted Sponge Cobalt

After a total of 1350 g of DMAPN had been added in Example 41, the DMAPN feed was stopped, the temperature lowered to room temperature and the pressure released. The activity test of Example 41 had shown that the catalyst was very active and with the added lithium hydroxide, although present at a low level (2.05 mmole LiOH/g catalyst) the catalyst was very selective as well. To see if sodium hydroxide would further improve the selectivity without affecting the hydrogenation rate, a fitting was removed and 1.64 g of NaOH (7.1 mmole/g of catalyst) dissolved in 5.67 g of water was injected with a syringe. The contents were stirred at 1200 rpm for 30 minutes and then all but 500 ml of the liquid reactor contents were removed through a sintered metal filter. After purging out air with nitrogen and nitrogen with hydrogen, the reactor was heated to 140° C. under moderate hydrogen pressure and then the pressure was again increased to 58 barg, the stirrer speed was increased to 1200 rpm and DMAPN (containing 2% water) fed again. The results are set forth in Table 14.

TABLE 14

Effect of Adding NaOH to LiOH Treated Sponge Cobalt Catalyst
normalized area %

| dmapn fed (g) | dmapn rate (g/min) | dmapn rate (g/g/hr)* | dma | mnpa | dmapa | dmapn | tmpda | 2°amine | others |
|---|---|---|---|---|---|---|---|---|---|
| 0.0 | 0.00 | 0 | 0.552 | 0.009 | 99.115 | 0.017 | 0.007 | 0.072 | 0.229 |
| 67.4 | 2.60 | 27 | 0.545 | 0.015 | 98.275 | 0.857 | 0.006 | 0.073 | 0.229 |
| 209.4 | 5.60 | 58 | 0.697 | 0.060 | 88.992 | 9.986 | 0.005 | 0.080 | 0.179 |

*Normalized feed rate = g DMAPN/g catalyst/hr

Table 14 shows the results of the addition of NaOH on an LIOH pretreated sponge cobalt catalyst. Here it is clear that even at the lowest feed rate the amount of unconverted DMAPN was significantly higher, i.e., 0.857% (after adding NaOH) vs 0.016% (before adding NaOH) and at 5.6 g/min the DMAPN concentration increased to almost 10%. The amount of 2°amine however remained low showing that NaOH may well influence the selectivity in a positive fashion, but at a high penalty with respect to rate.

EXAMPLE 43

Hydrogenation of DMAPN over Sponge Cobalt with Different Levels of Alkali Metal Hydroxides Added A series of runs was carried out to determine the effect of alkali metal hydroxide addition to a sponge cobalt catalyst. More specifically, a 2 liter Parr autoclave was charged with about 500 ml of DMAPN, about 10 g of water, about 2 g of a sponge catalyst pretreated with an aqueous solution of the alkali metal hydroxide at the level indicated in Table 15. The pretreatment was accomplished by adding the alkali metal hydroxide solution to a slurry of the catalyst in 100 ml of DMAPA followed by stirring for 5 to 30 minutes. The treated catalyst was then filtered, but not to dryness, then washed with 100 ml of DMAPA, filtered again, but not to dryness. The DMAPA wetted catalyst was then transferred to the autoclave as a wet paste. After purging out air the autoclave was heated to 100° C. at a hydrogen pressure of 750 psig (51 barg) and stirring speed of 1200 rpm. After the reaction time indicated in Table 15 the autoclave was cooled and vented. A sample was removed for gc analysis. The amount of DMAPN remaining and the amount of 2°amine formed was recorded. The conditions and results are shown in Table 15.

16 the autoclave was cooled and vented. A sample was removed for gc analysis. The amount of DMAPN remaining and the amount of 2°amine formed was recorded. The conditions and results are shown in Table 16.

TABLE 15

Effect of Alkali Metal Hydroxides on Activity and Selectivity

| Run | catalyst | catalyst amount g | alkali metal hydroxide MOH M | MOH amount g | MOH/ Catalyst mmoles/g | amount dmapn g | reaction time min | dmapn remaining wt % | 2°amine wt % |
|---|---|---|---|---|---|---|---|---|---|
| D1 | Co 2724 | 1.81 | lithium | 0.924 | 11.60 | 429.1 | 120 | 0.01 | 0.46 |
| D2 | Co 2724 | 2.06 | sodium | 0.743 | 8.65 | 428 | 140 | 86.0 | 0.42 |
| D3 | Co 2724 | 1.95 | potassium | 0.572 | 5.24 | 412.5 | 155 | 87.4 | 0.43 |
| D4 | Co 2700 | 1.85 | sodium | 0.706 | 9.54 | 427.8 | 185 | 88.0 | 0.23 |
| D5 | Ni 2800 | 2.51 | sodium | 0.696 | 6.93 | 432.4 | 120 | 94.7 | 0.33 |
| D6 | Co A8000* | 1.96 | sodium | 0.694 | 8.85 | 429.9 | 120 | 96.2 | 0.29 |
| D7 | Co 2700 | 2.19 | sodium | 0.508 | 5.80 | 426.7 | 260 | 86.9 | 0.24 |
| D8 | Co 2724 | 2.22 | sodium | 0.072 | 0.81 | 427.2 | 130 | 0.26 | 5.77 |
| D9 | Co 2724 | 2.11 | lithium | 0.261 | 2.81 | 429.0 | 140 | 0.12 | 0.60 |
| D10 | Co 2724 | 2.20 | lithium | 0.131 | 1.35 | 431.8 | 135 | 0.02 | 6.27 |
| D11 | Co 2724 | 2.04 | none | 0.000 | 0.00 | 433.7 | 125 | 0.12 | 9.34 |

*Activated Metal and Chemicals, Inc. All other catalyst in Table 15 are manufactured by W. R. Grace and Co.

Table 15 clearly shows that at alkali metal hydroxide levels over about 5 mmoles alkali metal hydroxide/g of catalyst only LiOH allowed the reaction to proceed to a high DMAPN conversion, i.e., a low DMAPN concentration within a reasonable time and also maintain a high selectivity to primary amine. Both NaOH and KOH at loadings of 5.24 to 9.54 mmoles/g of catalyst deactivated both promoted and unpromoted sponge cobalt and unpromoted sponge nickel catalysts to the extent that only about 4 to 14% of the DMAPN was converted to amines. At levels of about 1 mmole alkali metal hydroxide/g of promoted sponge cobalt, NaOH (run D8) and LiOH (run D10) showed an improved selectivity to primary amine over using the same catalyst without alkali metal hydroxide treatment (DI1) and all proceeded to near completion in about 125 to 135 minutes, however at as low as about 3 mmoles LiOH/g of catalyst (run D9), superior results were obtained with LiOH treated catalyst. Thus, to maintain a high rate of hydrogenation and high selectivity to primary amine, only LiOH at a high loading was effective.

EXAMPLE 44

Hydrogenation Of DMAPN Over Sponge Cobalt Treated External To The Reactor With Lithium Hydroxide In Solvents Other Than Nitriles Or Amines A 2 liter Parr autoclave was charged with about 500 ml of DMAPN, about 10 g of water, about 2 g of sponge cobalt catalyst (W. R. Grace and Co., Cobalt 2724) pretreated with an aqueous solution of lithium hydroxide at the level indicated in Table 16. The pretreatment was accomplished by adding the lithium hydroxide solution (about 1.0 g LiOH·H$_2$O/6.0 g water) to a slurry of the catalyst in 100 ml of a solvent (see Table 16 for specific solvent) followed by stirring for 5 to 30 minutes. The treated catalyst was then filtered, but not to dryness, then washed with 100 ml of the solvent and filtered again, but not to dryness. The solvent wetted catalyst was then transferred to the autoclave as a wet paste. After purging out air the autoclave was heated to 100° C. at a hydrogen pressure of 750 psig (51 barg) and stirring speed of 1200 rpm. After the reaction time indicated in Table

TABLE 16

Effect of Catalyst Pretreatment with LiOH by Solvents

| Run | Solvent | LiOH.H$_2$O/ Catalyst mmoles/g | amount dmapn g | reaction time min | dmapn remaining wt % | 2° amine wt % |
|---|---|---|---|---|---|---|
| B1 | water | 11.7 | 426.6 | 215 | 0.042 | 11.41 |
| B2 | methanol | 11.8 | 434.4 | 255 | 0.027 | 11.50 |
| B3 | ethanol | 11.1 | 430.0 | 180 | 0.046 | 8.87 |
| B4 | thf* | 11.3 | 439.2 | 145 | 0.103 | 0.95 |
| B5 | dmf* | 11.2 | 436.0 | 130 | 0.067 | 0.70 |

*thf = tetrahydrofuran; dmf = dimethylformamide

Table 16 shows that both selectivity and reaction rate are influenced by the solvent used to pretreat the sponge cobalt catalyst. Hydroxylic solvents, e.g., water and lower alcohols are not particularly suited as solvents for this purpose as can be seen by the large amount of secondary amine that is produced in runs B1, B2 and B3. Ethers (run B4) and amide solvents (run B5) on the other hand are good solvents for the pretreatment, as are amines and nitriles, shown in previous examples. On investigating this behavior, LiOH·H$_2$O was found to be quite soluble in water mixtures of both methanol and ethanol, but not in the same mixtures with dimethylformamide or tetrahydrofuran. Thus, solvents in which LiOH·H$_2$O is insoluble are suitable for the preparation of the lithium hydroxide-sponge cobalt catalysts described herein. Otherwise, on filtration of the slurry to recover the Raney cobalt catalyst, too much of the lithium hydroxide is washed from the catalyst.

EXAMPLES 45–49

Hydrogenation Of Acetonitrile Over Sponge Cobalt With Addition Of Alkali Metal Hydroxide.

A 300cc-stainless steel vessel (Autoclave Engineers) was charged with 1.0 g of sponge cobalt (W. R. Grace and Co, type 2724) catalyst (1% by wt.) and a mixture containing 98 g of acetonitrile, 2 g of water (2% by wt) (except Example 45) and 0.5 g (0.5% by wt) of the alkali metal hydroxide water (except Example 45 and 46). The pressure was lowered to 1 atm. and flushed with hydrogen several times. The temperature was increased to 100° C. at a heating rate of about 5° C./min, pressure of 15 psig $H_2$ and an agitator turning at approximately 30 RPM. At 100° C., the $H_2$ pressure was increased to 500 psig and the turbine agitator was accelerated to 1500 RPM. The reactor vessel pressure was maintained at 500 psig using hydrogen. GC samples are taken periodically. The reactants and conditions are set forth in Table 17 with the results in terms of selectivity and conversion are shown in Table 18.

TABLE 17

Results Of Hydrogenation Of Acetonitrile Over\ Sponge Cobalt Treated With Alkali Metal Hydroxides

| Example | 45 | 46 | 47 | 48 | 49 |
|---|---|---|---|---|---|
| Conditions | Anhydrous/ no alkali | 2% $H_2O$/ no alkali | 2% $H_2O$/0.5 wt % LiOH·$H_2O$ | 2% $H_2O$/0.5 wt % NaOH | 2% $H_2O$/0.5 wt % kOH |
| Alkali Addition Level (mmole alkali/g catalyst) | | | | | |
| | 0.00 | 0.00 | 11.4 | 12.5 | 8.9 |
| Rxn time (min) | ACETONITRILE CONVERSION (%) | | | | |
| 10 | 11.7 | 15.3 | 16.1 | 5.6 | 0 |
| 25 | 26.9 | 33.9 | 32.7 | 10.2 | 3.8 |
| 40 | 37.4 | 48.2 | 46.0 | 16.6 | 3.2 |
| 55 | 46.4 | 60.0 | 54.8 | 22.3 | 4.6 |
| 70 | 53.2 | 73.9 | 62.5 | 27.2 | 5.9 |
| 85 | 59.5 | 78.5 | 64.5 | 30.6 | 7.9 |
| 100 | 65.2 | 85.7 | 75.9 | 33.1 | 9.6 |
| 115 | 70.8 | 91.5 | 81.6 | 36.0 | 10.9 |
| 130 | 75.7 | 95.9 | 91.1 | 38.6 | |
| 145 | 80.2 | 98.8 | 91.8 | 41.2 | |
| 160 | 84.1 | 99.9 | 96.0 | 43.9 | |
| 175 | 88.0 | | 99.2 | 46.4 | |
| 190 | 91.4 | | 99.99 | 48.1 | |
| 205 | 94.5 | | | | |
| 220 | 96.5 | | | | |
| 235 | 98.9 | | | | |

As in previous examples, addition of water (Example 46) improved the rate of reaction as compared to Example 45. Added lithium hydroxide plus water (Example 47) gave a similar rate of reaction compared to Example 46 while both sodium hydroxide (Example 48) and potassium hydroxide (Example 49), added at similar or lower levels with benefit of added water, severely retarded the reaction.

TABLE 18

Effect of Lithium Hydroxide Treatment on Selectivity to Ethylamine

| Example | Water (wt %) | LiOH mmole/g catalyst | Conversion (%) | Ethylamine (wt %) | Diethylamine (wt %) | 2° imine (wt %) |
|---|---|---|---|---|---|---|
| 45 | 0 | 0 | 98.9 | 78.1 | 11.5 | 10.4 |
| 46 | 2 | 0 | 99.9 | 72.5 | 11.6 | 15.9 |
| 47 | 2 | 11.4 | 99.99 | 95.7 | 4.3 | 0.0 |

Table 18 shows that the selectivity to primary amine is dramatically improved by adding lithium hydroxide in Example 47 and that although water improved the rate of reaction in Example 46, the selectivity to primary amine was worse than when water was omitted (Example 45). The combination of a sponge cobalt catalyst pretreated with lithium hydroxide and addition of water produced a very good reaction rate and good selectivity as noted in Example 47 while similar treatment of the same catalyst with either sodium or potassium hydroxide gave very poor results.

EXAMPLE 50

Continuous Hydrogenation of DMAPN over Sponge Cobalt Treated with LIOH

A continuous hydrogenation of DMAPN was made in a stirred high pressure 600 ml autoclave containing an inlet for pumping in DMAPN, a level control device and an outlet for product. In this experiment 6.15 g sponge cobalt 2724 (W. R. Grace and Co.) and 2.09 g of LiOH·$H_2O$ (7.7 mmoles/g) was added to the autoclave and DMAPN feed which contained about 1.83% dimethylamine and 1.99% water was added at a rate of 5 g/min (46.9 g DMAPN/g catalyst/hr). The reactor was heated to a temperature of 140° C. while under a low hydrogen pressure and a slow stirring rate. When at 140° C., the pressure was increased to 59 barg (850 psig) and the agitation rate increased to 1000 rpm. The results are shown in Table 19.

TABLE 19

Continuous Hydrogenation Of DMAPN

| Time on Stream (hr) | DAMAPA | DMAPN | TMPDA | 2° AMINE | OTHER |
|---|---|---|---|---|---|
| | Normalized Area %* | | | | |
| 1.00 | 99.602 | 0.079 | 0.014 | 0.045 | 0.260 |
| 2.00 | 99.531 | 0.068 | 0.006 | 0.051 | 0.344 |
| 3.00 | 99.474 | 0.082 | 0.004 | 0.056 | 0.384 |
| 4.00 | 99.458 | 0.068 | 0.004 | 0.059 | 0.410 |
| 5.00 | 99.420 | 0.091 | 0.003 | 0.062 | 0.424 |
| 6.00 | 99.409 | 0.091 | 0.003 | 0.065 | 0.431 |
| 6.15 | 99.298 | 0.029 | 0.010 | 0.157 | 0.507 |
| 7.00 | 99.288 | 0.108 | 0.008 | 0.116 | 0.481 |
| 8.00 | 99.325 | 0.105 | 0.005 | 0.091 | 0.474 |
| 9.00 | 99.343 | 0.107 | 0.003 | 0.081 | 0.466 |
| 10.00 | 99.356 | 0.105 | 0.003 | 0.076 | 0.460 |
| 11.02 | 99.362 | 0.109 | 0.002 | 0.072 | 0.455 |
| 12.02 | 99.377 | 0.105 | 0.002 | 0.071 | 0.447 |

*Results exclude dimethylamine and water.

It is clear from these results that little change in selectivity occurred since the TMPDA and secondary amine concentrations remained essentially constant throughout 12 hours on stream. A slight rise and then fall of these concentrations occurred after 6 hours. This may be because the system was shut down over night and restarted the next day. The effect of LiOH appeared permanent with the sponge cobalt catalyst; continuous addition of LiOH was not required to maintain selectivity and reaction rate.

What is claimed is:

1. In a process for the catalytic hydrogenation of nitriles which comprises contacting the nitrile with hydrogen in the presence of a sponge cobalt catalyst under conditions for effecting conversion of the nitrile group to the primary amine, the improvement in the hydrogenation process which resides in effecting the hydrogenation in the presence of a sponge cobalt catalyst treated with a catalytic amount of lithium hydroxide and effecting the reaction in the presence of water.

2. The process of claim 1 wherein the nitrile is an aliphatic nitrile having from 1–30 carbon atoms.

3. The process of claim 1 wherein the lithium hydroxide is present in the sponge cobalt catalyst in an amount of from 0.1 to 100 millimoles lithium hydroxide per gram of sponge cobalt catalyst.

4. The process of claim 3 wherein the water is present in an amount from 0.1 to 25% by weight of the nitrile to be hydrogenated.

5. The process of claim 4 wherein the aliphatic nitrile is an alkyl nitrile having from 1 to 30 carbon atoms.

6. The process of claim 5 wherein the alkyl nitrile is selected from the group consisting of acetonitrile, propionitrile, butyronitrile; lauronitrile, stearonitrile, succinonitrile, methylglutaronitrile and adiponitrile.

7. The process of claim 4 wherein the aliphatic nitrile is a β-aminonitrile or a β-alkoxynitrile.

8. The process of claim 7 wherein the nitrile is a β-aminonitrile selected from the group consisting of: β-aminopropionitrile, di-(2-cyanoethyl)amine, N-methyl-β-aminopropionitrile, N,N-dimethyl-β-aminopropionitrile, N-ethyl-β-aminopropionitrile, N,N-diethyl-β-aminopropionitrile, mono-(2-cyanoethyl)methylamine; di-(2-cyanoethyl)methylamine, N-(2-cyanoethyl) ethanolamine, N,N-di-(2-cyanoethyl)ethanolamine, N-(2-cyanoethyl)diethanolamine and N-(2-cyanoethyl) propanolamine.

9. The process of claim 4 wherein the lithium hydroxide is present in an amount of from 2 to 30 millieqivalents per gram of sponge cobalt catalyst.

10. The process of claim 9 wherein the water is present in an amount of from 0.3 to 8% by weight of the nitrile to be hydrogenated.

11. The process of claim 4 wherein the aliphatic nitrile is selected from the group consisting of isophoronenitrile, 3-hydroxypropionitrile and acrylonitrile.

12. The process of claim 4 wherein the aliphatic nitrile is an alkoxy nitrile represented by the formula:

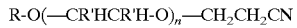

where R=$C_1$ to $C_{30}$ alkyl radical, R'=H or $C_1$ to $C_8$ alkyl radical and n =1 to 30.

13. The process of claim 12 wherein the alkoxy nitrile is selected from the group consisting of methoxypropionitrile, bis-cyanoethylether, mono-(2-cyanoethyl)ethylene glycol; bis-(2-cyanoethyl)ethyleneglycol, mono-(2-cyanoethyl) diethyleneglycol; bis-(2-cyanoethyl)diethyleneglycol; bis(2-cyanoethyl)tetramethyleneglycol and di-(cyanoethylethylamine.

14. The process of claim 4 wherein the nitrile is an α-aminonitrile selected from the group consisting of aminoacetonitrile, imino-bis-acetonitrile and nitrilotriacetonitrile.

15. The process of claim 3 wherein the nitrile is a $C_{7-1}$ aromatic nitrile.

16. The process of claim 15 wherein the aromatic nitrile is selected from the group consisting of isophthalonitrile, terephthalonitrile, benzonitrile and benzyl cyanide.

17. The process of claim 4 wherein the nitrile is a cyanoethylated amide represented by the formula; $RCON(CH_2CH_2CN)_n$ where R is H or a $C_{1-8}$ alkyl radical and n is 1 or 2.

18. The process of claim 17 wherein the cyanoethylated amide is selected from the group consisting of cyanoethylated acetamide and cyanoethylated propionamide.

19. The process of claim 4 wherein the nitrile is a cyanoethylated lactam represented by the formula: $(CH_2)_m CONCH_2CH_2CN$ where m is 3, 4 or 5.

20. The process of claim 4 wherein the cyanoethylated lactam is N-cyanoethyl caprolactam.

21. The process of claim 4 wherein the nitrile is a cyanoethylated urea represented by the formula: $R_2NCONR_2$ where R=H, $C_1$-$C_8$ alkyl radical or $CH_2CH_2CN$.

22. The process of claim 21 wherein the cyanoethylated urea is N-cyanoethyl urea.

23. The process of claim 7 wherein the aliphatic nitrile is a cyanoethylether formed by reaction of acrylonitrile with an alcohol, a glycol, or a glycol ether.

24. The process of claim 7 wherein the aliphatic nitrile is a β-amino nitrile formed by the reaction of acrylonitrile and a $C_{1-30}$ alkylamine or $C_{1-8}$ alkundamine.

* * * * *

UNITED STATES PATENT AND TRADEMARK OFFICE
CERTIFICATE OF CORRECTION

PATENT NO. : 5,869,653
DATED : 9 February 1999
INVENTOR(S) : Thomas Albert Johnson It is certified that error appears in the above-identified patent and that said Letters Patent is hereby corrected as shown below:

Column 22, line 8, "$C_{7-1}$" should be "$C_{7-15}$".

Column 22, line 36, "alkanolamine" should be "alkylamine"

Signed and Sealed this

Eighteenth Day of January, 2000

Attest:

Attesting Officer

Q. TODD DICKINSON

Commissioner of Patents and Trademarks